(12) United States Patent
Eells et al.

(10) Patent No.: US 8,496,645 B2
(45) Date of Patent: Jul. 30, 2013

(54) SUTURE WINDING FOR A DRAINAGE CATHETER

(75) Inventors: Robert M. Eells, Bloomington, IN (US); Scott E. Eells, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 61 days.

(21) Appl. No.: 13/147,971

(22) PCT Filed: Feb. 2, 2010

(86) PCT No.: PCT/US2010/022814
§ 371 (c)(1),
(2), (4) Date: Aug. 4, 2011

(87) PCT Pub. No.: WO2010/090982
PCT Pub. Date: Aug. 12, 2010

(65) Prior Publication Data
US 2011/0295237 A1    Dec. 1, 2011

Related U.S. Application Data (60) Provisional application No. 61/150,468, filed on Feb. 6, 2009.

(51) Int. Cl.
*A61M 1/00* (2006.01)
(52) U.S. Cl.
USPC ........... 604/540; 604/264; 604/523; 604/528; 604/534; 604/535; 604/905; 285/305
(58) Field of Classification Search
USPC ................... 604/533, 534, 535, 540
See application file for complete search history.

(56) References Cited

U.S. PATENT DOCUMENTS

| | | | |
|---|---|---|---|
| 4,643,720 | A | 2/1987 | Lanciano |
| 4,740,195 | A | 4/1988 | Lanciano |
| 5,041,085 | A | 8/1991 | Osborne et al. |
| 5,185,004 | A | 2/1993 | Lashinski |
| 5,342,198 | A | 8/1994 | Vassiliadis et al. |
| 5,419,764 | A | 5/1995 | Roll |
| 5,522,400 | A | 6/1996 | Williams |
| 5,599,291 | A | 2/1997 | Balbierz et al. |
| 5,928,208 | A | 7/1999 | Chu et al. |

(Continued)

FOREIGN PATENT DOCUMENTS

| | | |
|---|---|---|
| EP | 0 368 473 A2 | 10/1989 |
| WO | WO 99/10039 | 3/1999 |
| WO | WO 99/11315 | 3/1999 |
| WO | WO 2008/021596 A1 | 2/2008 |

OTHER PUBLICATIONS

Notification of Publication of International Application mailed Aug. 12, 2010, for related patent application PCT/US2010/022814.

*Primary Examiner* — Tatyana Zalukaeva
*Assistant Examiner* — Ilya Treyger
(74) *Attorney, Agent, or Firm* — Brinks Hofer Gilson and Lione (57) ABSTRACT

Drainage catheters for use in a variety of medical procedures are presented herein. The drainage catheter features an improved tension member locking mechanism. In use, once the drainage catheter is placed as desired, a second connector piece is rotated relative to a first connector piece to wind the tension member around a spooling region and pull the distal end of the catheter tube into a locked configuration. Once the tension member is tensioned, the first and second connector pieces are pulled into a locking engagement thereby securing the catheter tube in the locked configuration.

20 Claims, 6 Drawing Sheets

U.S. PATENT DOCUMENTS

| | | |
|---|---|---|
| 5,941,849 A | 8/1999 | Amos, Jr. et al. |
| 6,042,577 A | 3/2000 | Chu et al. |
| 6,110,183 A | 8/2000 | Cope |
| 6,159,177 A | 12/2000 | Amos, Jr. et al. |
| 6,231,542 B1 | 5/2001 | Amos, Jr. et al. |
| 6,508,789 B1 | 1/2003 | Sinnott et al. |
| 6,547,761 B2 | 4/2003 | Liu |
| 6,673,060 B1 | 1/2004 | Fleming, III |
| 6,699,233 B2 | 3/2004 | Slanda et al. |
| 7,083,595 B2 | 8/2006 | Chu et al. |
| 7,192,415 B2 | 3/2007 | Sauvageau |
| 7,217,256 B2 | 5/2007 | Di Palma |
| 2001/0049490 A1 | 12/2001 | Slanda et al. |
| 2007/0032779 A1 | 2/2007 | Accisano, III et al. |
| 2007/0078385 A1 | 4/2007 | Accisano, III et al. |
| 2007/0083154 A1 | 4/2007 | Sauvageau |
| 2007/0083189 A1 | 4/2007 | Lampropoulos et al. |
| 2007/0088259 A1 | 4/2007 | Chu et al. |

SUTURE WINDING FOR A DRAINAGE CATHETER

This application claims the benefit under 35 U.S.C. §365 as a national application of PCT Application No. US2010/022814, filed Feb. 2, 2010, and claims the benefit under 35 U.S.C. §119(e) of U.S. Provisional Application No. 61/150,468, filed Feb. 6, 2009, both of which are hereby incorporated by reference herein.

TECHNICAL FIELD

The present invention generally relates to medical devices and specifically to medical devices intended for draining fluids from parts of human or animal bodies. In particular, the present invention relates to mechanisms for tightening a tension member used in drainage catheters.

BACKGROUND

The present invention relates generally to catheters and particularly to a lockable connector for drawing and maintaining the distal end of a catheter into a desired locked configuration.

Physicians currently use stabilizing structures to immobilize catheters and tubes within various body lumens, including the gastro-intestinal tract and the biliary duct. For example, suprapubic catheterization of the bladder is used to drain the bladder after surgery or when the genitourinary system is obstructed. Percutaneously inserted catheters are also used to drain the kidney or biliary system as well as to drain abscesses, or other areas of fluid collection, and other viscera. Still other percutaneously inserted catheters are employed as gastrostomy feeding tubes.

Typically, these catheters are introduced into the patient by means of a large hypodermic needle or trocar, which pierces the abdominal wall. A wire guide is inserted through the needle and then the needle is removed. A catheter tube having a stiffening cannula positioned therein is then passed over the wire guide into the cavity. The cannula and wire guide are then withdrawn, leaving the catheter in the desired cavity.

With respect to the bladder, the advantage of this technique is that irritation and infection of the urinary tract is minimized. However, one problem with these catheters is that the catheter may be easily pulled out by body movement, or by emptying of, for example, the bladder. Another problem is that side ports at the distal end of the catheter may be inadvertently drawn into the abdominal cavity, creating the potential for severe infections.

Various catheters have been developed with so-called pigtail loops at their distal ends for ensuring drainage of the cavity and preventing accidental removal therefrom. Generally, the pigtail loop is formed by pulling on a first end of a flexible tension member, for example, a suture, which extends through an inner lumen of the catheter. The second end of the tension member is secured to or within the catheter. The first end of the tensile member extends out of a first aperture near the distal end of the catheter and is looped back into the catheter through a second aperture disposed proximal of the first aperture. The first end of the tension member is then directed through the lumen towards the proximal end of the catheter for tightening. When the tensile member is pulled, it causes the distal end of the catheter to bend and assume a "pigtail" shape, which is larger than the aperture opened by the trocar, thus preventing the catheter from being accidentally removed.

While the pigtail configuration is commonly used to obtain the locked configuration of the distal end of the catheter, other configurations may also be used. For example, another locking configuration involves a catheter with axial cuts that subdivide the catheter tube into several sections. In these catheters, a tension member, such as a suture, attaches to the catheter tube at the distal end of the axial cuts, and when the tension member is tensioned the catheter axially shortens and the cut portions flare out to form an anchoring device. Regardless of whether a flared anchor or pigtail loop is used, the first end of the tension member may be held in place by any one of a number of retention means.

For example, the first end of the flexible tension member may be secured by axially placing a hollow cap into or over the first end of the catheter tube, thus trapping the flexible tension member in place and allowing the protruding first end to be cut. A problem with this catheter design is that once the protruding first end of the flexible tension member is cut, the hollow cap may slip or be inadvertently removed. As a result, the shortened flexible tension member moves distally, releases the pigtail, and is either difficult or impossible to retrieve. In another case, the flexible tension member is trapped between two or more hollow tubes, one of which is slidably inserted axially into the other. A short length of the flexible member is generally left hanging from the catheter tube so that if the flexible tension member becomes loose, it may be retightened. Alternatively, an external sleeve is slid over the flexible tension member protruding from the side of the catheter tube. This external sleeve may be located within an external locking device in which a lever arm with a cam may be used to press the sleeve tightly against the tension member to lock it in place. Disadvantageously, such devices enlarge the profile of the drainage catheter and require additional connections, thereby complicating the drainage procedure. Therefore, a need exists for a secure, easy to use, low profile tension member locking mechanism for use with drainage catheters.

BRIEF SUMMARY

In one aspect of the present invention, a drainage catheter is provided that includes a catheter tube having distal and proximal ends, and a central lumen. The distal end may assume an insertable configuration or a locked configuration. A first connector piece is attached to the proximal end of the catheter tube. The first connector piece includes a first lumen that is contiguous with the central lumen. A second connector piece is insertably attachable to the first connector piece. The second connector piece includes a second lumen contiguous with the first lumen and the central lumen. A sealing tube is disposed partially within a first slot in the first connector piece and partially within a second slot of the second connector piece. A tension member is at least partially disposed through the central lumen, first lumen and second lumen. The tension member has first and second ends, and at least one of the first and second ends is attached to the second connector piece. The first connector piece includes a spooling region, whereby a portion of the tension member adjacent the first end of the tension member is wound around the spooling region. The tension member is tensioned by rotation of the second connector piece relative to the first connector piece while the first and second connector pieces are pushed towards one another in an axial direction. The tensioning of the tension member causes the distal end of the catheter tube to assume the locked configuration.

In another embodiment of the present invention, a drainage catheter is provided that includes a catheter tube having a central lumen, and distal and proximal ends. The distal end may assume an insertable configuration or a locked configuration. A first connector piece is attached to the proximal end of the catheter tube. The first connector piece includes a first lumen that is contiguous with the central lumen, and a first lumen wall that is formed along a portion of the first lumen. A second connector piece is insertably attachable to the first connector piece. The second connector piece includes a second lumen contiguous with the first lumen and the central lumen. A sealing tube is disposed partially within a first slot in the first connector piece and partially within a second slot of the second connector piece. A tension member is at least partially disposed through the central lumen, first lumen and second lumen. The tension member has a first end and a second end, wherein at least one of the first and second ends is attached to the second connector piece. A spooling member is rotatably disposed around the first lumen wall whereby a portion of the tension member adjacent the first end of the tension member is wound around the spooling member. The tension member is tensioned by rotation of the second connector piece relative to the first connector piece while the first and second connector pieces are pushed towards one another in an axial direction. The tensioning of the tension member causes the distal end of the catheter tube to assume the locked configuration.

DETAILED DESCRIPTION

Figure 1:
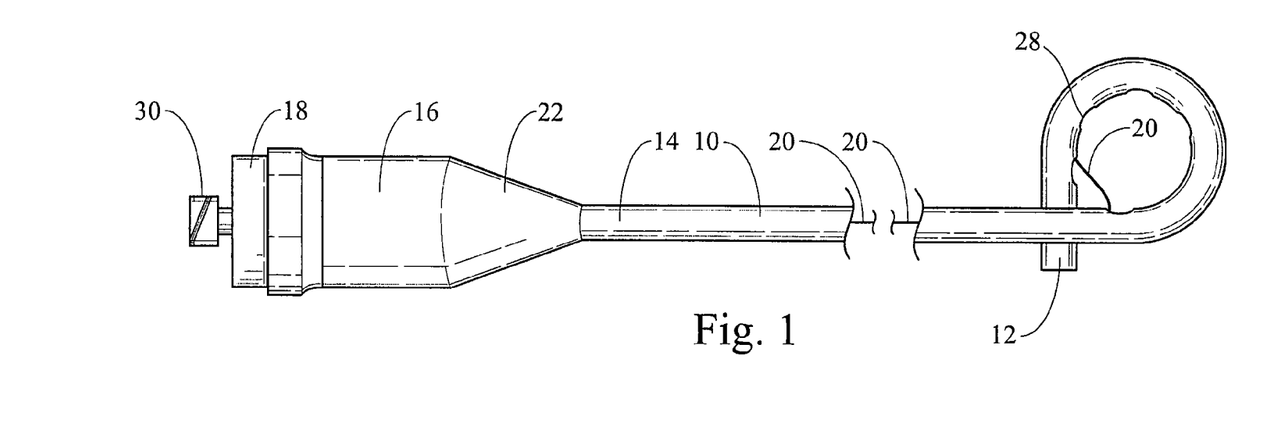
FIG. 1 shows an illustrative embodiment of the drainage catheter, with the distal end of the catheter tube in a locked configuration.
Figure 2:
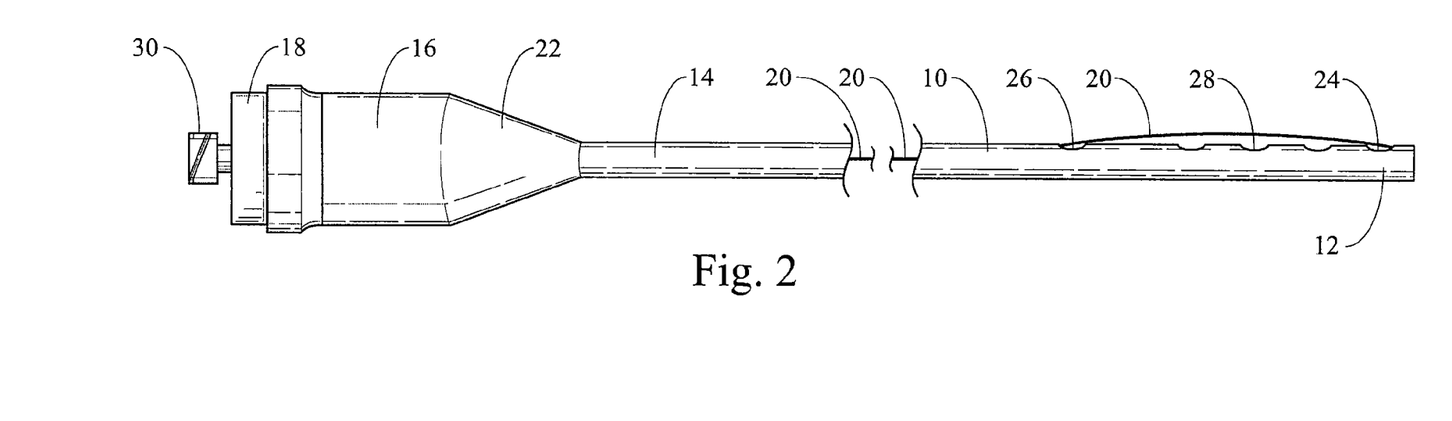
FIG. 2 shows another view of an illustrative embodiment of the drainage catheter with the distal end of the catheter tube in the insertable configuration.

In accordance with one embodiment of the drainage catheter claimed herein, and as shown in FIGS. 1 and 2, the drainage catheter includes a catheter tube 10 having distal and proximal ends 12, 14, a first connecting piece 16, a second connecting piece 18, and a tension member 20. The proximal end 14 of the catheter tube 10 is attached to the first connector piece 16 at a transitional connection 22. The transitional connection 22 may be accomplished using a ferrule, adhesive, frictional fit, clamps, a threaded connector, or in other manners known to those skilled in the art. In this embodiment, the distal end of the catheter tube includes a distal opening 24. A proximal opening 26 is located proximal of the distal opening 24, i.e., nearer the middle of the catheter tube 10. In some embodiments, a plurality of openings 28 will be arrayed between the distal opening 24 and proximal opening 26. Additional openings may also be placed proximal of the proximal opening 26, or the additional openings 28 may be omitted all together. In some embodiments, the most proximal portion of the second connector piece 18 includes a luer connector 30 as shown in FIGS. 1 and 2. However, it should be understood that such a connector is not required. Additionally, while not shown, those skilled in the art will understand that a tapered tip may be attached to the distal most portion of the catheter tube 10. Such a tapered tip may assist with the insertion of the catheter, and, in particular, may help prevent accordioning of the catheter.

Figure 3:
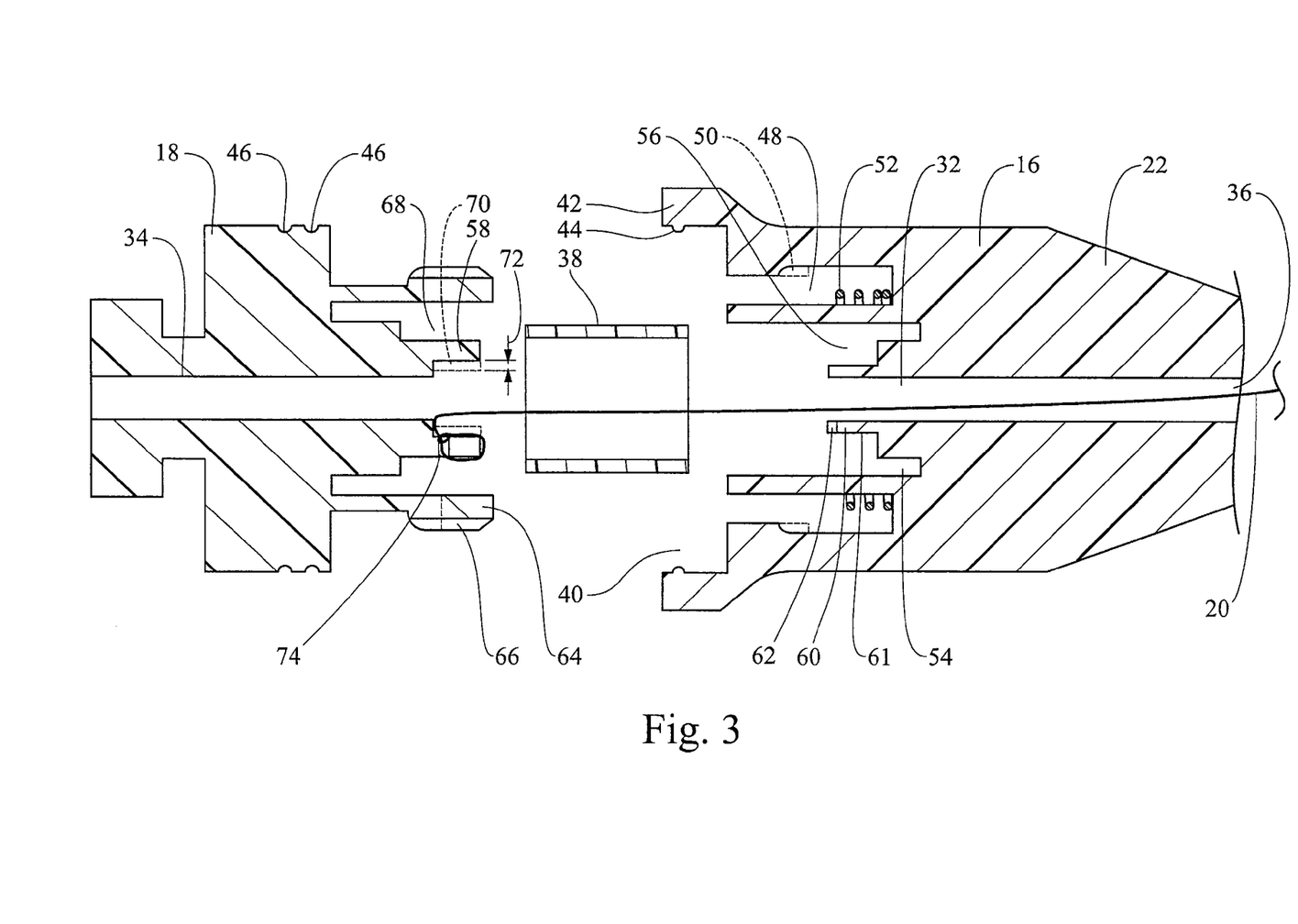
FIG. 3 shows an exploded cross sectional view of an embodiment of the first and second connector pieces of a drainage catheter.

FIG. 3 depicts a cross-sectional close up exploded view of a portion of an embodiment of the drainage catheter. As visible in this figure, the first and second connection pieces 16 and 18 include a plurality of annular slots as well as first and second lumens 32, 34, respectively. When assembled, the first and second lumens 32, 34 are contiguous with the central lumen 36 of the catheter tube. In addition to the first and second connector pieces 16, 18, the drainage catheter includes a sealing tube 38. The various annular slots of the first and second connectors 16, 18, as well as the interaction between the first and second connectors 16, 18 and sealing tube 38 of the illustrated embodiment, are described in more detail below.

The first connector piece 16 includes a receiving opening 40, defined by a cylindrical outer wall 42, which is configured to receive the second connector piece 18. In some embodiments, the cylindrical outer wall 42 may include a sealing ring 44 configured to engage receiving grooves 46 on the second connecting piece 18. Although not shown, it should be understood that the sealing ring could alternatively be disposed on the second connector element 18 and the receiving grooves could be formed in the cylindrical outer wall 42. The first connector piece 16 also includes a 360 degree annular slot 48. In some embodiments, the annular slot includes female ratchet pieces 50 formed in the outermost wall of the annular slot 48. In the embodiment illustrated in FIG. 3, the female ratchet pieces 50 consist of a plurality of splines distributed uniformly around the periphery of the outermost wall of the annular slot 48. In some embodiments, the annular slot 48 includes a spring 52 to bias the first and second connector pieces away from one another, as described further below. The first connector piece 16 also includes a first sealing slot 54 configured to receive the sealing tube 38. A second lumen slot 56 is located adjacent to the sealing slot 54. The second lumen slot 56 is configured to receive the second lumen wall 58 of the second connector piece 18 when the drainage catheter is assembled. The first lumen 32 is defined at the proximal end of the first connector piece 16 by a first lumen wall 60. The embodiment of the drainage catheter depicted in FIG. 3 includes a notch 62 formed in the first lumen wall 60. This notch 62 is intended to accommodate the tension member 20 as explained more fully below. When assembled, the outer surface of the first lumen wall 60 forms a spooling region 61 about which the tension member 20 is wrapped as it is tensioned.

The second connector piece 18 includes male ratchet pieces 64 that are configured to engage with the annular slot 48 and female ratchet pieces 50 of the first connector piece 16. In the embodiment depicted in FIG. 3, the male ratchet pieces 64 include flared extensions 66. These flared extensions 66 are described in greater detail in conjunction with FIGS. 4 through 6 below. The second connector piece 18 includes a second sealing slot 68 adjacent to the male ratchet pieces 64. Like the first sealing slot 54 described above, the second sealing slot 68 is configured to accommodate the sealing tube 38. The second lumen wall 58 is located adjacent to the second sealing slot 68. In this embodiment, the second lumen wall 58 has an inner radius that is larger than the outer radius of the first lumen wall 60 and, when assembled, the first and second lumen walls 58, 60 define a gap 70 (illustrated by the horizontal dashed lines in parallel to the second lumen wall 58 in FIG. 3). The size 72 of this gap 70 is defined by the difference between the outer radius of the first lumen wall 60 and the second lumen wall 58. The gap 70 is described more fully in association with FIGS. 7-9 below. The second lumen wall 58 includes a hole 74. In the embodiment shown in FIG. 3, the tension member 20 passes through the central lumen 36, into the first lumen 32, around the second lumen wall 58, through the hole 72, through the second lumen 34, and then loops loosely around the tension member 20 adjacent the distal end of the second lumen wall 58. Those skilled in the art understand that the tension member 20 may connect to the second connector piece 18 in any number of ways in addition to the manner described and shown herein.

Figure 4:
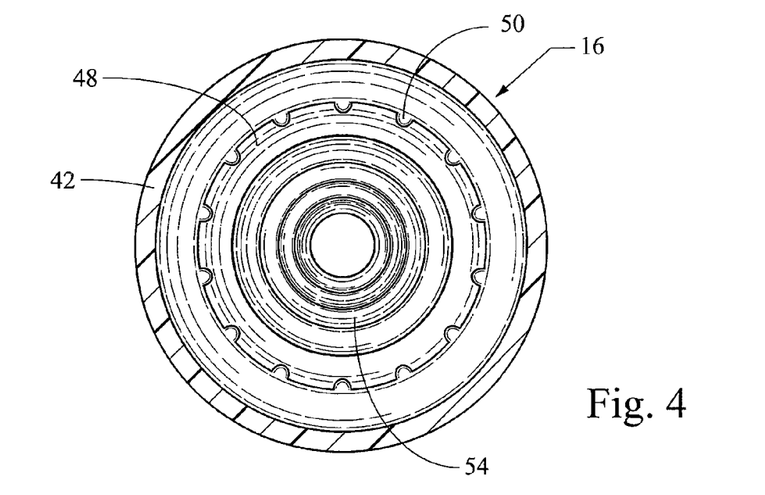
FIG. 4 shows a head-on view of the proximal end of an embodiment of the first connector piece.
Figure 5:
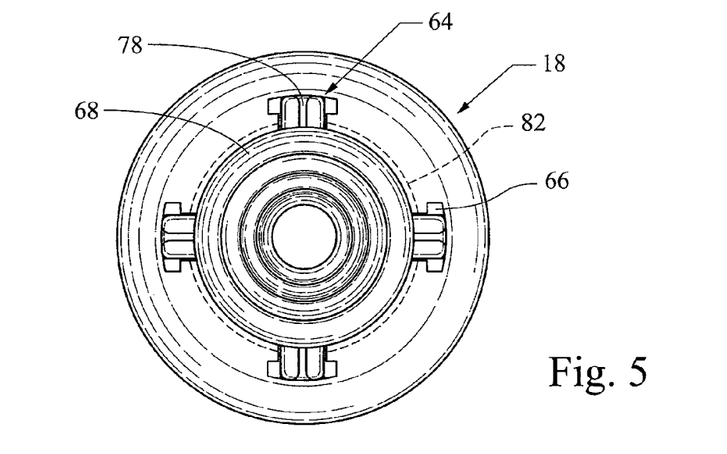
FIG. 5 shows a head-on view of the distal end of an embodiment of the second connector piece.

FIGS. 4 and 5 depict end on views of the first and second connector pieces, respectively. As depicted in FIG. 4, the female ratchet pieces consist of splines depending from the outer wall of the annular slot 48. The female ratchet pieces 50 define openings into which the male ratchet pieces are inserted. Furthermore, the first and second connector pieces are disposed away from one another in their axial directions (generally by the spring 52 or compressed sealing tube 38, however biasing may be accomplished by other mechanisms). This axial force generally causes cutouts 76 (visible in FIG. 6) formed in the male ratchet piece to engage the female ratchet pieces 50, thereby locking the first and second connector pieces 16, 18 together with respect to relative rotation.

Figure 6:
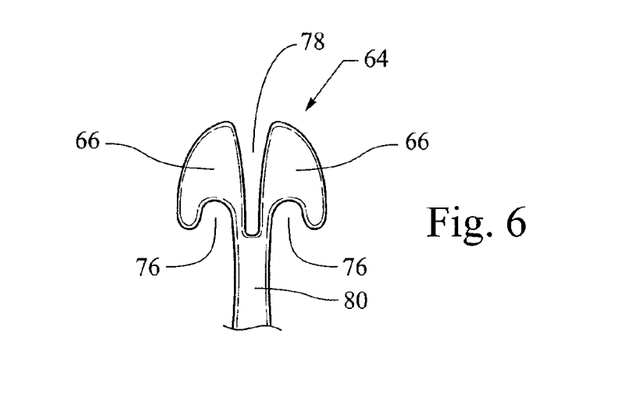
FIG. 6 shows a bird's eye view of an embodiment of one of the male ratchet pieces of the second connector piece.

As visible in the embodiment of the second connector piece 18 illustrated in FIG. 5, the male ratchet pieces 64 are tapered towards their front ends to simplify insertion of the male ratchet pieces 64 into the annular groove and female ratchet pieces 50 of the first connector piece 16. Furthermore, the male ratchet pieces 64 have a central slit 78 cut therein to allow the flared extensions 66 to compress and fit within the narrower openings defined by the female ratchet pieces 50. FIG. 6 provides a bird's eye view of one of the male ratchet pieces 64 of the present embodiment. As visible in FIG. 6, the male ratchet piece 64 includes a portion having the flared extensions 66, as well as a stem 80. From FIGS. 3 and 5, it should be clear that the stem 80 connects the portion of the male ratchet piece 64 with the flared extensions 66 to the rest of the second connector piece 18. Although the stems are depicted only as independent extensions, it should be understood that in some embodiments the stem may form an annular ring along a portion of its length, as shown by a ring of dashed lines 82 in FIG. 5. Such an annular ring 82 may be desirable in helping to confine the sealing tube 38, thereby advantageously improving the seal between the central lumen 36, first lumen 32 and second lumen 34 and the male and female ratchet pieces 50, 64 and the annular slot 48. Furthermore, by confining the sealing tube 38, such an annular ring 82 may assist the sealing tube 38 in biasing the first and second connector pieces 16, 18 away from one another.

Figure 7:
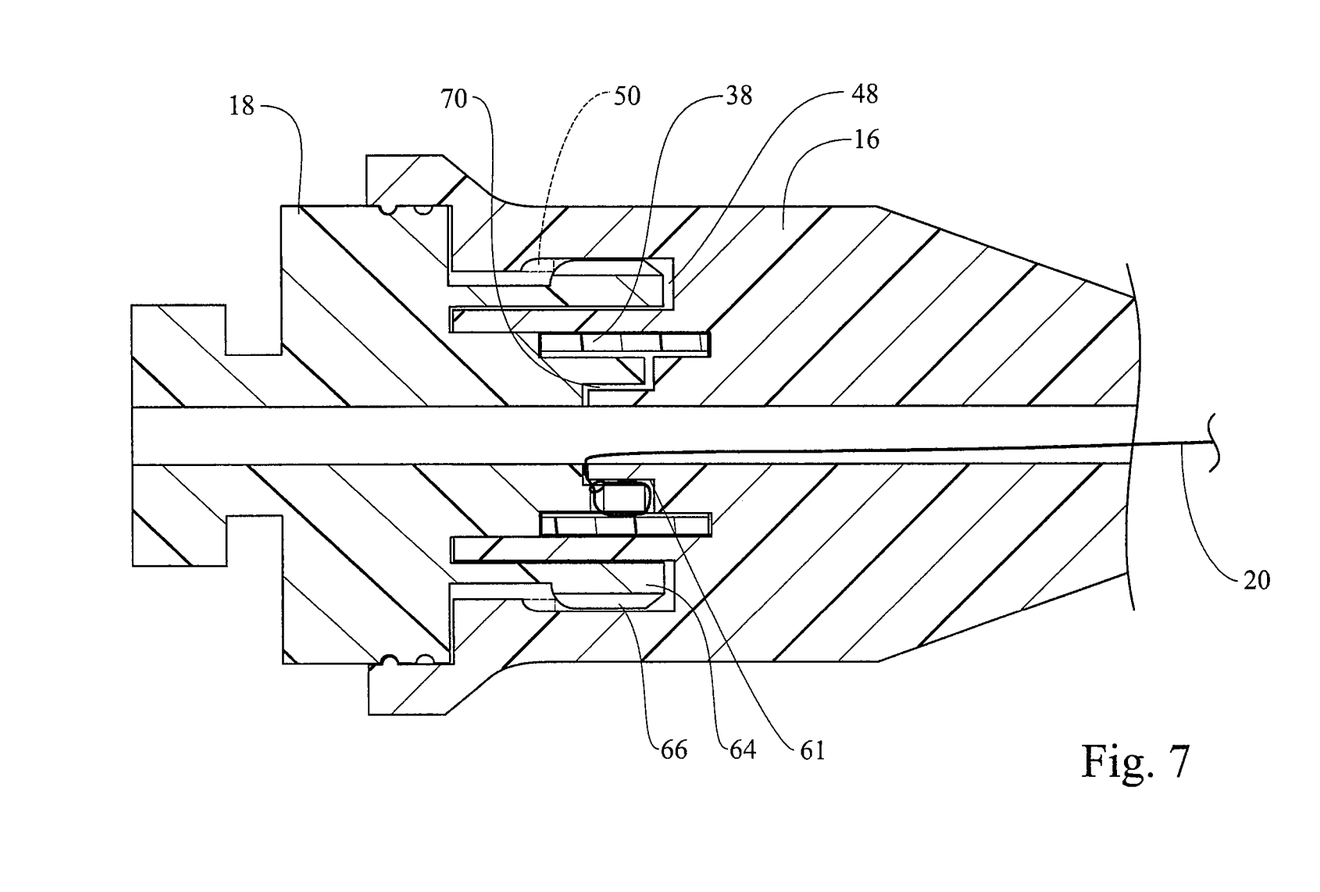
FIG. 7 shows a cross-sectional view of an embodiment of the assembled first and second connector pieces.
Figure 8:
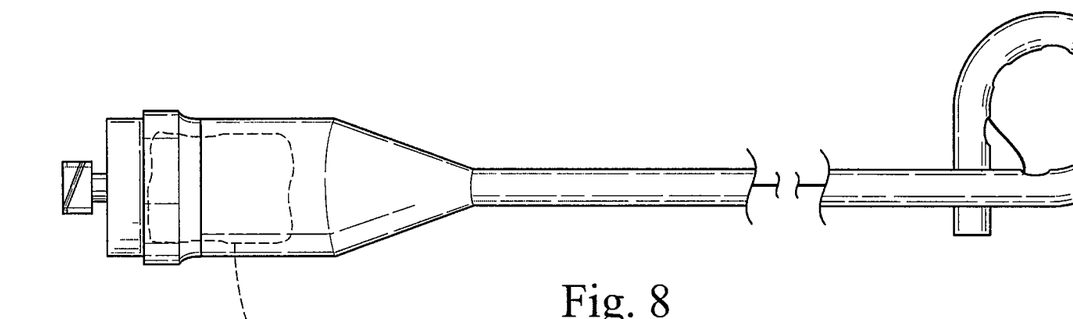
FIG. 8 shows an embodiment of the drainage catheter with an indication for the enlarged hidden view shown in FIG. 9.
Figure 9:
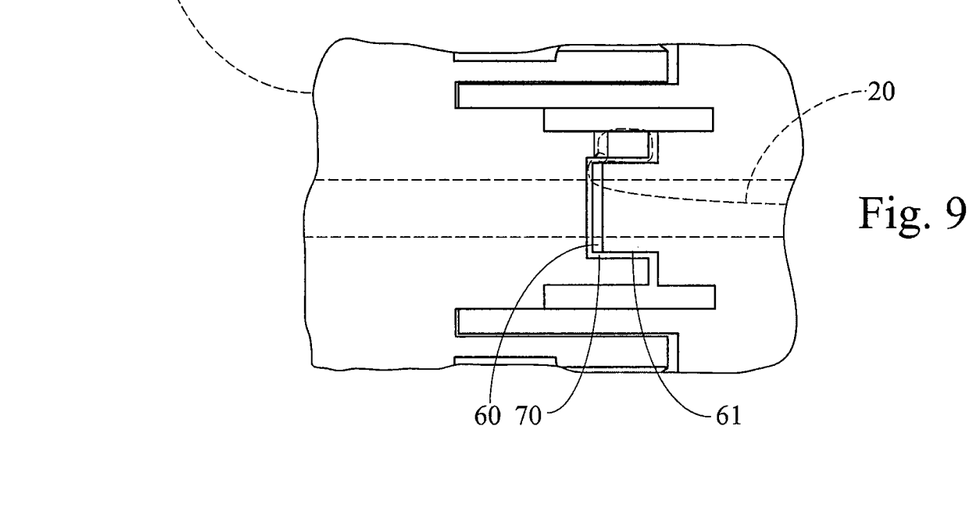
FIG. 9 is an enlarged hidden view of an embodiment with the tension member winding around the spooling region.

FIG. 7 is an assembled cross-sectional view of the first and second connector pieces 16, 18 of one embodiment of the drainage catheter. As visible in this figure, the first and second connector pieces 16, 18 have been pushed towards one another in their axial directions so that they may be rotated relative to one another to tension the tension member 20. By pushing the first and second connector pieces 16, 18 towards one another, the male ratchet pieces 64 are disengaged from the female ratchet pieces 50. In the embodiment of FIG. 7, no spring is required in the annular slot 48 of the first connector piece 16. Instead, the sealing tube 38 provides sufficient axial force to bias the first and second connector pieces away from one another absent an outside axially compressive force. The gap 70 between the inner surface of the second lumen wall and the first lumen wall is visible in this figure. As shown in FIG. 9, which is a cutaway view of the area indicated by dashed lines in FIG. 8, this gap 70 provides space in which the tension member 20 may be wound about the spooling region 61.

Referring to FIGS. 1, 2 and 7-9, the manner of use of one embodiment of the drainage catheter is described. As shown in FIG. 2, the drainage catheter is initially disposed in a relaxed, insertable configuration. The physician then may insert a stiffening cannula, trocar, or other introducing device (not shown) into the lumen of the drainage catheter and position the catheter into the desired portion of a patient's body. After positioning, the introducer device is removed. For instance, for a procedure intended for a blocked biliary gland, the physician may insert the drainage catheter percutaneously into the patient. The physician may then push the distal end of the catheter tube past the blockage in the biliary duct. Thereafter, the physician needs to secure the drainage catheter in place. To do so, the physician first pushes the first and second connector pieces 16, 18 towards one another and then secondly begins to rotate the second connector piece 18 relative to the first connector piece 16 while holding the first and second connector pieces 16, 18 pushed towards one another. As shown in FIG. 9, this relative rotation between the second connector piece 18 and first connector piece 16 causes the tension member 20 to be wrapped around the spooling region 61 of the first lumen wall 60. Advantageously, as the physician begins to rotate the second connector piece 18 with respect to the first connector piece 16, the physician will notice a little resistance as the male ratchet pieces 64 are disengaged from the female ratchet pieces 50. Furthermore, depending on the tolerances and the force within which the physician pushes the first and second connector pieces 16, 18 towards one another, the physician may receive a tactile response upon beginning relative rotation of the first and second connector pieces 16, 18 as the male and female ratchet pieces 64, 50 pass one another.

As visible in FIG. 2, the tension member 20 extends from where it is connected to the second connector piece, through the first lumen 32 (see FIG. 3) and central lumen 36 to the proximal opening 26 of the catheter tube 10. The tension member then emerges from the central lumen 36 through the proximal opening 26 before reentering the central lumen through the distal opening 24. The second end of the tension member 20 may be secured within the central lumen or elsewhere in or on the drainage catheter. When the physician tensions the tension member 20 by rotating the second connector piece 18 relative to the first connector piece 16, the distal end 12 of the catheter tube 10 is pulled into the locked configuration as shown in FIGS. 1 and 8. As the physician tensions the tension member 20, the physician gets tactile feedback regarding the state of the distal end 12 of the catheter tube 10. When resistance to rotation increases, the physician knows that the distal end 12 is in the locked configuration. At this point, the physician pulls the first and second connector pieces 16, 18 in a direction away from one another thereby helping engage the male ratchet pieces 64 with the female ratchet pieces 50 in a locked position. Thereafter, the first and second connector pieces 16, 18 are maintained in this position by the biasing force provided within the drainage catheter. This biasing force may be provided by the sealing tube 38, the spring 52, or other means as described above.

Figure 10:
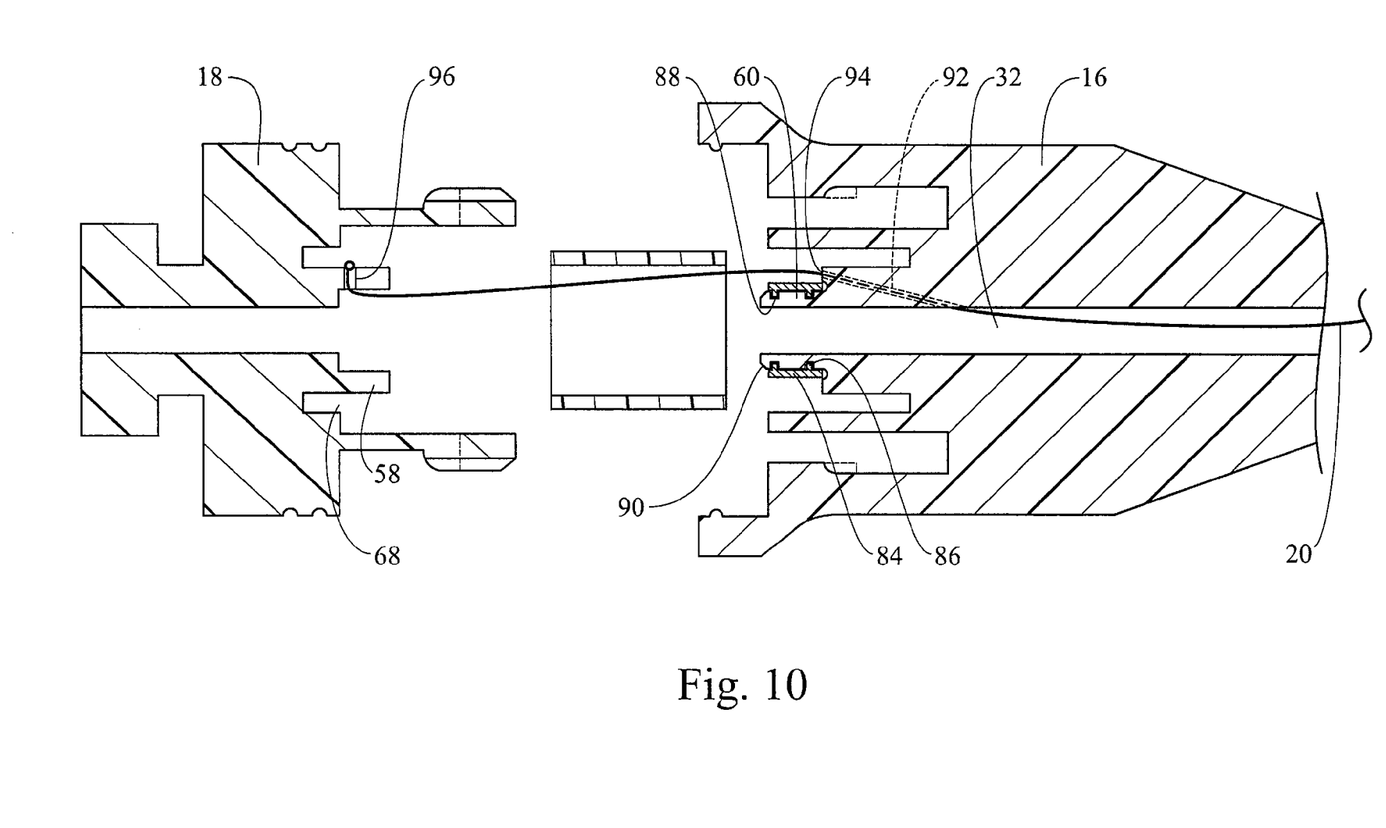
FIG. 10 shows a cross-sectional view of an alternate embodiment of the drainage catheter winding mechanism.

An alternate embodiment of the drainage catheter is illustrated in cross-section in FIG. 10. In this embodiment, an additional freely rotating spooling member 84 is placed on the first lumen wall 60. As shown in FIG. 10, the spooling member 84 includes annular ribs 86 that engage with indentations 88 formed in the outer surface of the first lumen wall 60. Additionally, the first lumen wall 60 includes a small ramp over which the spooling member 84 is forced when placed onto the first lumen wall. Both the ramp 90 and annular ribs 86 and indentations 88 help keep the spooling member 84 on the first lumen wall 60. However, those skilled in the art understand that the annular ribs 86, indentations 88, and ramp 90 are not required, and that the spooling member 84 may be used without these features.

The first connector piece 16 includes a small lumen 92 through which the tension member 20 passes from the first lumen 32 to an opening 94 just above the spooling member 84. The tension member 20 then passes through an aperture 96 in the second lumen wall 58. The tension member 20 may be affixed to the second connector piece 18, for example by attaching a bead to the first end of the tension member 20. In a preferred embodiment, this bead (not shown) may fit within an enlarged portion (not shown) of the aperture 96 so as not to extend into the second sealing slot 68. However, other means of securing the first end of the tension member 20 may be used.

In operation, the embodiment shown in FIG. 10 works much like the embodiments shown in FIGS. 1-9 and described above. The device is positioned into the targeted tissue in the same manner as the other embodiments described above. However, the actual winding of the tension member 20 differs slightly. In this embodiment, as the second connector piece 18 is rotated relative to the first connector piece 16, the tension member 20 begins to wind around the spooling member 84. As the tension member 20 winds around the spooling member 84, friction may increase. Because the spooling member 84 freely rotates on the first lumen wall 60, the spooling member 84 may rotate with the second connector piece 18 as friction builds between the tension member 20 and the spooling member 84. In this manner, the tension member 20 may more easily be pulled from the distal end of the catheter tube 12 because additional winding does not require the tension member be dragged about the spooling surface over the entire spooled length of tension member. Instead, all of the newly spooled tension member is drawn from the direction of the distal end of the catheter tube 12. This allows the physician to more easily position the distal end of the catheter tube 12 into the locked configuration as shown in FIGS. 2 and 8.

While the embodiment depicted in FIGS. 1, 2 and 8 is a pigtail catheter, it should be understood that other configurations may be used. It is only necessary that the catheter have an insertable configuration and a locked configuration, wherein a tension member is utilized to configure the catheter in the locked configuration. Therefore, other types of catheters, such as axially contracting and radially expanding anchoring tips are within the scope of the present disclosure.

The drainage catheter disclosed herein will generally be made from plastic or polymeric materials. For instance, in the preferred embodiment, the catheter tube consists of a urethane material. The first and second connector pieces also may be made of plastic or polymeric materials. However, other materials may be used for both the catheter tube and first and second connector pieces. In another preferred embodiment, the catheter tube is made from a urethane material, and the distal end of the catheter is coated with a hydrophilic material. In another embodiment, a radiopaque marker is included on the drainage catheter adjacent to the most proximal opening. The radiopaque marker assists the physician in identifying when the drainage catheter has been properly placed within the patient. The sealing tube disclosed herein may be made from any number of polymeric materials. In one preferred embodiment, the sealing tube consists of a silicon material. The tension member is composed of materials known to be suitable to those skilled in the art. Often, the tension member will consist of a suture, which may be made from a variety of materials including wires, plastics, and polymers among others.

It should be understood that the present drainage catheter may be used in a number of medical procedures, including, but not limited to, biliary drainage, nephrostomy, suprapubic bladder drainage, and abscess drainage. Furthermore, it should be understood that the present drainage catheter may be used for applications in which the body fluids are drained externally of the body or internally within the body. Advantageously, because the proximal end of the tension member is confined within the drainage catheter, and because no additional components are required to maintain the locked configuration, the device achieves a smaller overall profile. This smaller profile may be particularly advantageous for internal drainage applications.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

The invention claimed is:

1. A drainage catheter comprising: a catheter tube having distal and proximal ends, a central lumen, and wherein the distal end is configurable between an insertable configuration and a locked configuration;

a first connector piece attached to the proximal end of the catheter tube, the first connector piece including a first central lumen that is contiguous with the central lumen;

a second connector piece insertably attachable to the first connector piece, the second connector piece including a second central lumen contiguous with the first central lumen and the central lumen;

a sealing tube disposed partially within a first slot in the first connector piece and partially within a second slot of the second connector piece;

a tension member, at least partially disposed through the central lumen and first central lumen, the tension member having first and second ends, one of the first and second ends being attached to the second connector piece;

a spooling region disposed between (a) the first connector piece and the second connector piece and (b) between the first and second central lumens and the sealing tube; and wherein the tension member is tensioned by rotation of the first connector piece relative to the second connector piece while the first and second connector pieces are moved relative to one another in a first axial direction, whereby a portion of the tension member is wound around the spooling region to lock the tension member in a locked position, and the tensioning of the tension member causes the distal end of the catheter tube to move from the insertable configuration to the locked configuration.

2. The catheter of claim 1 wherein the spooling region further comprises a spooling member having a tubular shape, the spooling member being rotatable relative to the first connector piece, whereby a portion of the tension member adjacent the first end of the tension member is wound around the spooling member.

3. The drainage catheter of claim 1 wherein the first connector piece comprises an auxiliary lumen separate from the first central lumen, through which the tension member passes from the first central lumen to a tension member opening proximate to the spooling region.

4. The catheter of claim 1 wherein the catheter tube further comprises a distal opening near the distal end of the catheter tube and a proximal opening proximal of the distal opening; wherein the tension member passes through the distal opening and the proximal opening, the tension member extending along the exterior of the catheter tube between the distal and proximal openings; and wherein the locked configuration further comprises a pigtail configuration.

5. The catheter of claim 1 wherein the second connector piece further comprises one of a male ratchet piece or an annular slot for receiving the male connector piece, the first connector piece comprises the other of the male ratchet piece and annular slot for receiving the male connector piece, the annular slot further comprises a female ratchet piece, and wherein the male ratchet piece is lockably engageable with the female ratchet piece by moving the first connector piece in a second axial direction relative to the second connector piece.

6. The catheter of claim 5 wherein the female ratchet piece further comprises a plurality of splines uniformly disposed around the perimeter of the annular slot.

7. The catheter of claim 5 wherein the sealing tube is disposed between the first and second central lumens and the male and female ratchet pieces.

8. The catheter of claim 5 wherein the sealing tube is dimensioned to provide biasing force to dispose the first connector piece in the second axial direction relative to the second connector piece.

9. The catheter of claim 5 further comprising a spring to bias the first connector piece in the second axial direction relative to the second connector piece.

10. The catheter of claim 5 further comprising an outer sealing ring formed on an outer portion of one of the first or second connector pieces, the sealing ring engaging a sealing groove formed on the other of the first or second connector pieces.

11. The catheter of claim 5 wherein the sealing tube is disposed between the first and second central lumens and the male and female ratchet pieces, and the sealing tube is dimensioned to provide biasing force to dispose the first connector piece in the second axial direction relative to the second connector piece.

12. The catheter of claim 11 wherein the female ratchet piece further comprises a plurality of splines uniformly disposed around the perimeter of the annular slot.

13. The catheter of claim 12 further comprising an outer sealing ring formed on an outer portion of one of the first or second connector pieces, the sealing ring engaging a sealing groove formed on the other of the first or second connector pieces.

14. The catheter of claim 12 wherein the catheter tube further comprises a distal opening near the distal end of the catheter tube and a proximal opening proximal of the distal opening; wherein the tension member passes through the distal opening and the proximal opening, the tension member extending along the exterior of the catheter tube between the distal and proximal openings; and wherein the locked configuration further comprises a pigtail configuration.

15. The catheter of claim 5 wherein the female ratchet piece further comprises a plurality of splines uniformly disposed around the perimeter of the annular slot, and further comprising a spring to bias the first connector piece in the second axial direction relative to the second connector piece.

16. The catheter of claim 15 further comprising an outer sealing ring formed on an outer portion of one of the first or second connector pieces, the sealing ring engaging a sealing groove formed on the other of the first or second connector pieces.

17. The catheter of claim 1 wherein the spooling region further comprises a spooling member having a tubular shape, the spooling member being rotatable relative to the first connector piece, whereby a portion of the tension member adjacent the first end of the tension member is wound around the spooling member, and the first connector piece comprises an auxiliary lumen separate from the first central lumen, through which the tension member passes from the first central lumen to a tension member opening proximate to the spooling region.

18. The catheter of claim 1 wherein the sealing tube is dimensioned to provide biasing force to dispose the first connector piece in a second axial direction relative to the second connector piece.

19. The catheter of claim 1 further comprising a spring to bias the first connector piece in the second axial direction relative to a second connector piece.

20. The catheter of claim 1 further comprising an outer sealing ring formed on an outer portion of one of the first or second connector pieces, the sealing ring engaging a sealing groove formed on the other of the first or second connector pieces.

* * * * *